US00PP11352P

United States Patent [19]

Murakami

[11] Patent Number: Plant 11,352

[45] Date of Patent: Apr. 18, 2000

[54] PETUNIA PLANT NAMED 'SUNBELKIST'

[75] Inventor: Yasuyuki Murakami, Shiga, Japan

[73] Assignee: Suntory Limited, Osaka, Japan

[21] Appl. No.: 09/007,056

[22] Filed: Jan. 14, 1998

[30] Foreign Application Priority Data

Nov. 25, 1997 [JP] Japan ..... 10362

[51] Int. Cl.[7] ..... A01H 5/00

[52] U.S. Cl. ..... Plt./356

[58] Field of Search ..... Plt./356

[56] References Cited

U.S. PATENT DOCUMENTS

| | | | |
|---|---|---|---|
| P.P. 6,899 | 7/1989 | Tsuda et al. | Plt./356 |
| P.P. 6,914 | 7/1989 | Tsuda et al. | Plt./356 |
| P.P. 6,915 | 7/1989 | Tsuda et al. | Plt./356 |
| P.P. 8,489 | 12/1993 | Hirabayashi et al. | Plt./356 |
| P.P. 8,768 | 6/1994 | Hirabayashi et al. | Plt./356 |
| P.P. 9,322 | 10/1995 | Tachibana et al. | Plt./356 |
| P.P. 9,341 | 10/1995 | Tachibana et al. | Plt./356 |
| P.P. 9,342 | 10/1995 | Sakazaki et al. | Plt./356 |
| P.P. 9,556 | 5/1996 | Tachibana et al. | Plt./356 |
| P.P. 9,557 | 5/1996 | Suzuki et al. | Plt./356 |
| P.P. 9,754 | 12/1996 | Suzuki et al. | Plt./356 |
| P.P. 10,278 | 3/1998 | Murakami | Plt./356 |
| P.P. 10,279 | 3/1998 | Murakami | Plt./356 |
| P.P. 10,287 | 3/1998 | Murakami | Plt./356 |
| P.P. 10,355 | 4/1998 | Murakami | Plt./356 |

*Primary Examiner*—Howard J. Locker
*Assistant Examiner*—Wendy Anne Baker
*Attorney, Agent, or Firm*—Burns, Doane, Swecker & Mathis, L.L.P.

[57] ABSTRACT

Disclosed herein is a Petunia plant, having a semi-decumbent growth habit and long stems. The Petunia plant has abundant branching, with strong secondary branching, and a great profusion of blooms. The whole bush remains in bloom for a considerable period of time. The flowers are single and very small, the bi-colored petals have a vivid purplish red streak on a brilliant yellow base color. The bottom coloration of the corolla throat is strong yellow and the outside color of the corolla tube is light greenish yellow. The plant has a high resistance to rain, heat, drought and pests such as mites and aphids.

2 Drawing Sheets

BACKGROUND OF THE VARIETY

The Petunia is a very popular plant and is used for flower bedding and potting in the summer season. There are only a few varieties of Petunia plants which do not have an upright growth habit and which have a high resistance to rain, heat, cold, and diseases. Some known Petunia varieties, i.e., the Revolution series 'Revolution Purplepink' (U.S. Plant Pat. No. 6,915), 'Revolution Brilliantpink' (U.S. Plant Pat. No. 6,914), 'Revolution Brilliantpink-Mini' (U.S. Plant Pat. No. 6,899) are of this decumbent type, have long stems, a lower plant height, abundant branching, and a high resistance to heat, cold and rain. However, there are only a few varieties having a great profusion of very small yellow flowers, and a high resistance to rain, heat, cold and diseases. Accordingly, this invention was aimed at obtaining a new variety having a variegated pattern on a yellow ground colored petal and a very small flower, together with the above features.

The new variety of Petunia plant according to this invention originated as a mutant sport occurring as a spontaneous variant of 'Sunbelchipi' (U.S. Plant Pat. No. 10,355).

The new variety of Petunia plant was discovered as a sport of 'Sunbelchipi' in April, 1997 at the Oumi Nursery Center of SUNTORY Ltd., at 863-1, Aza-Iketani, Oomori-cho, Youkaiti-shi, Shiga-ken, Japan. The discovered Petunia plant was propagated by cuttings in April, 1997, and then grown in beds and pots on trial beginning in June, 1997 at the Plant Biotechnology Laboratory of SUNTORY Ltd., Kitakoma-gun, Yamanashi-ken, Japan. The botanical characteristics of the plant were examined, using the parent variety, 'Sunbelchipi', for comparison. As a result, it was concluded that this Petunia is distinguishable from any other variety, whose existence is known to us, and is uniform and stable in its characteristics. This new variety of Petunia plant was named 'Sunbelkist' (*Petunia hybrida*).

'Sunbelchipi', the parent cultivar of the instant plant, was obtained as follows:

First of all, 167 seedlings were obtained from crossing a wild type of Petunia plant called 'C1' as the female parent and another wild type of Petunia plant called 'C2' as the pollen parent in November, 1992. From this crossing 15 seedlings were selected in view of their decumbent growth habit and flower coloration in spring, 1993. 30 seedlings were obtained from a crossing of these selected 15 seedlings in summer, 1993 and were grown. Then 16 seedlings were selected from these 30 seedlings. These selected 16 seedlings were tested in a trial by flower potting and bedding. The botanical characteristics of the finally-selected 16 plants were then examined, using the similar variety 'Pearl Sky Blue' (non-patented in the United States) for comparison, from spring, 1994 to spring, 1995. Finally, only one Petunia plant was selected in April, 1995. As a result, it was concluded that this Petunia is distinguishable from any other variety, whose existence is known to us, and is uniform and stable in its characteristics. This new variety of Petunia plant was named 'Sunbelchipi'.

The female parent used in the crossing of 'Sunbelchipi' was a wild type of Petunia plant called 'C1' (♀) native to Brazil, the seeds of which were gathered at Gramado, Rio Grande Do Sul, Brazil and introduced to Japan in January, 1992. The Petunia plant 'C1' has an erect habit, abundant branching and a great profusion of blooms. The flowers are single, small and have purplish pink colored petals. The leaf shape is elliptic. The Petunia plant 'C1' has a high resistance to rain, heat, drought and pests.

The pollen parent used in the crossing of 'Sunbelchipi' was another wild type of Petunia plant called 'C2' (♂) also native to Brazil, the seeds of which were gathered at Gramado, Rio Grande Do Sul, Brazil and introduced to Japan in January, 1992. The Petunia plant 'C2' has a semi-decumbent habit, long stems, abundant branching and a great profusion of blooms. The flowers are single, very small and have reddish purple petals. The leaf shape is lanceolate. The Petunia plant 'C2' has a high resistance to rain, heat, drought and pests. These wild type of Petunia plants 'C1' and 'C2', and 'Sunbelchipi', are presently maintained at the Oumi Nursery Center of SUNTORY Ltd., at 863-1, Aza-Iketani, Oomori-cho, Youkaiti-shi, Shiga-ken, Japan.

In the following description, the color-coding is in accordance with the Horticultural Colour Chart of The Royal Horticultural Society, London, England (R.H.S. Colour Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

The characteristics of the similar variety 'Pearl Sky Blue', used for examination as a comparison, are as follows.

Plant:
- *Growth habit.*—Medium upright.
- *Plant height.*—14 cm.
- *Spreading area of plant.*—15–17 cm in diameter.
- *Blooming period.*—April to September in the southern Kanto area, Japan.

Stem:
- *Thickness.*—2.7 mm.
- *Pubescence.*—Dense.
- *Branching.*—Abundant.
- *Length of internode.*—1.3 cm.

Leaf:
- *Shape.*—Elliptic.
- *Length.* (*average*)—5.5 cm.
- *Width.* (*average*)—3.5 cm.
- *Color.*—Strong yellow green (R.H.S. 144A, JHS 3507).
- *Pubescence.*—Dense.
- *Thickness.*—0.5–0.6 mm.
- *Leaf attaching angle to stem.*—Horizontal to droopy.

Flower:
- *Facing direction.*—Upward.
- *Type.*—Single.
- *Shape.*—Funnel-shaped, with five-fissured limb.
- *Shape of petal tip.*—Obtuse.
- *Waving of petal.*—Weak.
- *Lobation of petal.*—Shallow.
- *Diameter.*—5.5 cm.
- *Color.*—Petal: Strong bluish purple (R.H.S. 88B-76D, JHS 8310). Bottom color of the corolla throat and the outside color of corolla tube: light yellow green (R.H.S. 4C, JHS 3304).
- *Reproductive organs.*—1 normal pistil and 5 normal stamens.
- *Peduncle.*—0.7–0.9 mm in thickness, and 2.7 cm in length.

Physiological and ecological characteristics: Moderate resistance to heat, cold and diseases and pests. Strong resistance to rain.

The botanical characteristics of the Petunia plant 'Sunbelchipi', the parent of this new variety, 'Sunbelkist', are as follows.

Growth habit: Decumbent to medium.

Plant height: 15–16 cm.

Spreading area of plant: The stem extends to a length of 11–13 cm from the base.

Growth: Very vigorous with abundant branching, a great profusion of blooms; the whole bush remaining in bloom for a considerable period of time.

Blooming period: April to late October in the southern Kanto area, Japan.

The plant shape does not change throughout this period.

Stem:
- *Thickness.*—2.3 mm.
- *Pubescence.*—Present.
- *Branching.*—Abundant. Secondary branching is very strong.
- *Length of internode.*—1.4 cm.

Leaf:
- *Shape.*—Lanceolate.
- *Length.*—5.1 cm.
- *Width.*—1.6 cm.
- *Color.*—Dark yellow green. (R.H.S. 146B, JHS 3508).
- *Thickness.*—0.2–0.4 mm.
- *Pubescence.*—Sparse.
- *Leaf attaching angle to stem.*—Slanted upward to horizontal.

Flower:
- *Facing direction.*—Horizontal.
- *Type.*—Single.
- *Shape.*—Funnel-shape, with five-fissured limb.
- *Shape of petal tip.*—Between obtuse and acute.
- *Waving of petal.*—Weak.
- *Lobation of petal.*—Shallow.
- *Diameter.*—2.8–2.9 cm.
- *Color.*—Petal: Vivid purplish red (R.H.S. 66B, JHS 9707). Bottom color of the corolla throat: Strong yellow (R.H.S. 11A., JHS 2513). Outside color of corolla tube: Light greenish yellow (R.H.S. 4C, JHS 2904).
- *Reproductive organs.*—1 normal pistil and 5 normal stamens.
- *Peduncle.*—0.7–0.8 mm in thickness, and 1.9 cm in length.

Physiological and ecological characteristics: High resistance to rain, heat, drought and pests, especially resistance to rain and heat is very strong.

This new and distinct variety of Petunia plant, 'Sunbelkist', was asexually reproduced by cuttings at the aforementioned the Plant Biotechnology Laboratory of SUNTORY Ltd., Kitakoma-gun, Yamanashi-ken, Japan. and the homogeneity and stability thereof were confirmed.

SUMMARY OF THE VARIETY

The new variety of Petunia plant 'Sunbelkist' has a semi-decumbent growth habit, long stems and a vivid purplish red streak (mist) pattern on a brilliant yellow base color of the flower petals and thus is very different from a similar variety, 'Pearl Sky Blue'. The plant has a semi-decumbent growth habit, the plant shape is compact, with abundant branching and a great profusion blooms, and the whole bush remains in bloom for a considerable period of time. The secondary branching is especially strong. The flowers are single and very small, which is clearly different from the small flowers of 'Pearl Sky Blue' and the petals are a bright yellow with purplish red variegation, which is clearly different from the strong bluish purple of 'Pearl Sky Blue'. The parent 'Sunbelchipi' has a single colored petal, with a vivid purplish red petal coloration and a strong yellow bottom coloration at the corolla throat. The new variety 'Sunbelkist' has bi-colored petals and a vivid purplish red streak (mist) pattern on a brilliant yellow base color and a strong yellow bottom coloration at the corolla throat and thus is very different from 'Sunbelchipi'.

DESCRIPTION OF THE VARIETY

Figure 1:
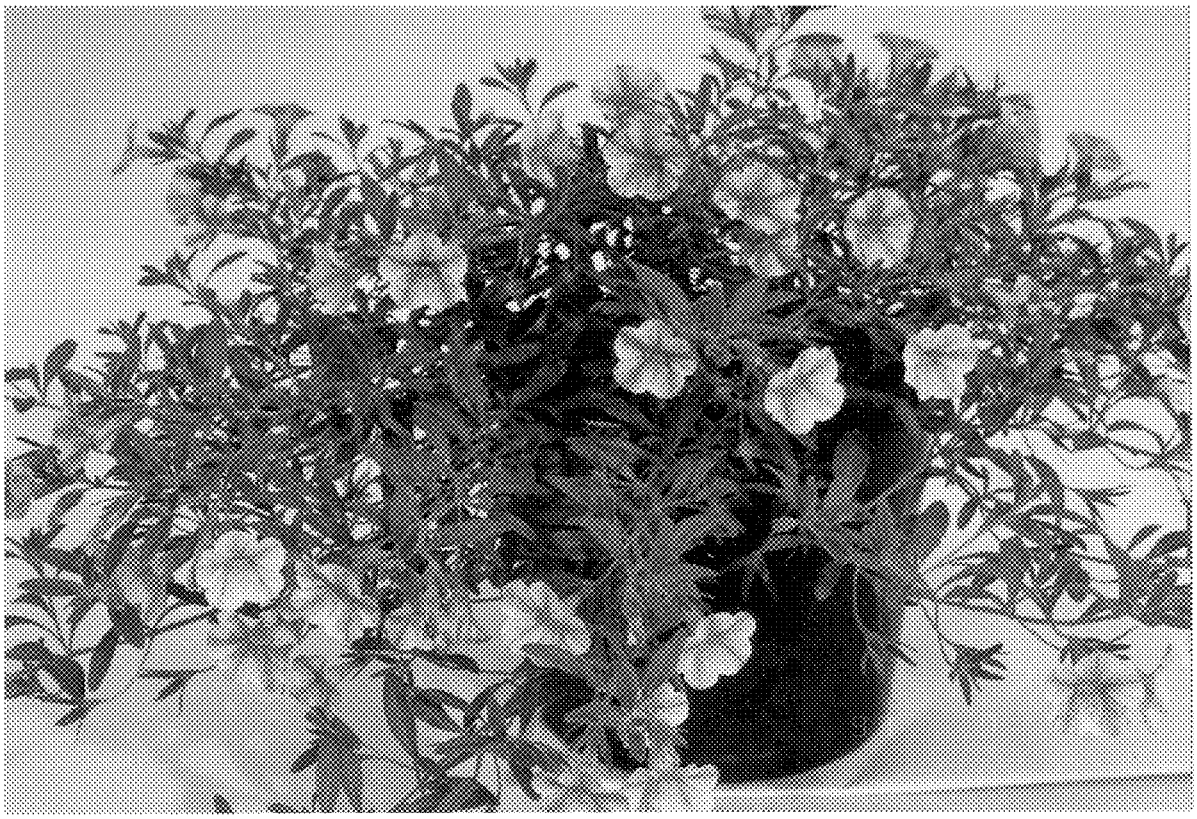
FIG. 1 is a photograph giving a partial view of the new variety of Petunia plant planted in a flower pot.
Figure 2:
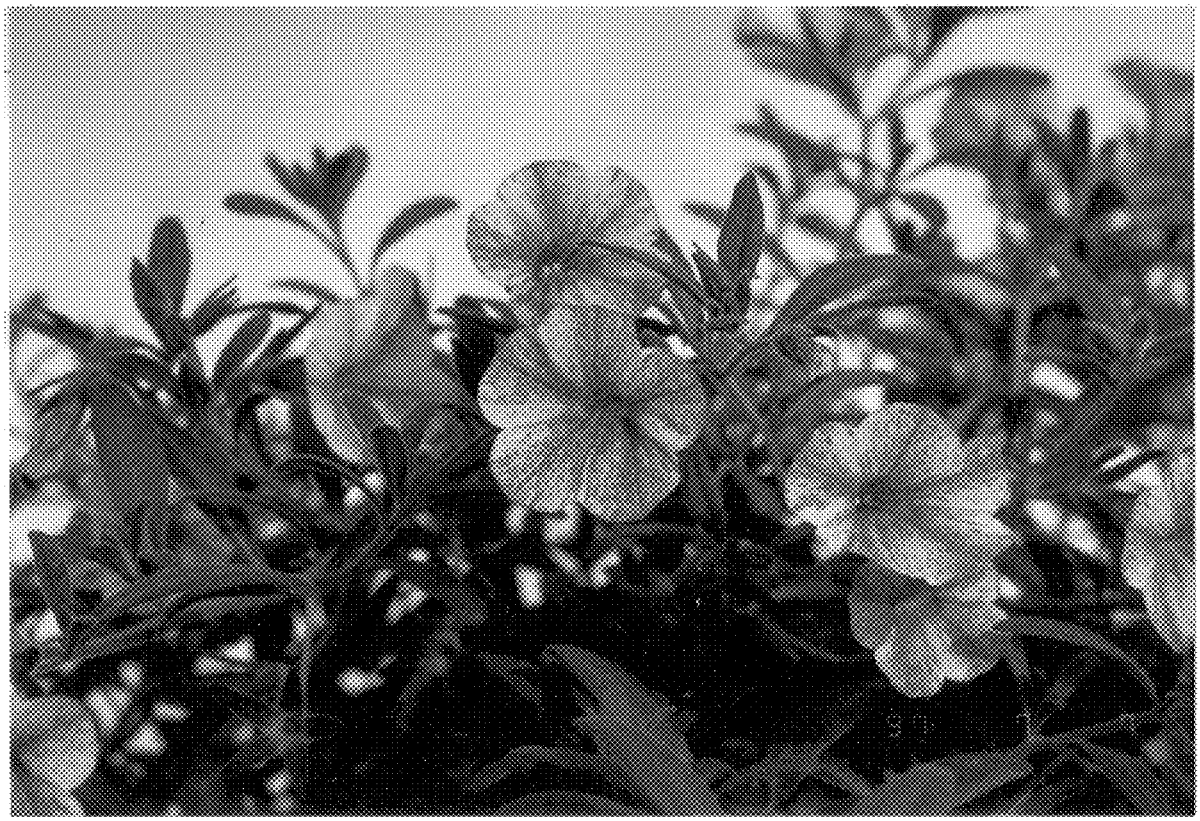
FIG. 2 is a photograph of flowers of the new variety of Petunia plant.

The botanical characteristics of the new and distinct variety of Petunia plant 'Sunbelkist' are as follows.

Plant:

*Growth habit.*—Decumbent to medium upright.

*Plant height.*—17 cm.

*Spreading area of plant.*—The stem extends to a length of 19 cm from the base.

*Growth.*—Very vigorous with abundant branching, a great profusion of blooms; the whole bush remaining in bloom for a considerable period of time.

*Blooming period.*—April to late October in the southern Kanto area, Japan. The plant shape does not change throughout this period.

Stem:

*Thickness.*—22 mm.

*Pubescence.*—Present.

*Branching.*—Abundant. Secondary branching is very strong.

*Length of internode.*—1.4 cm.

Leaf:

*Shape.*—Lanceolate.

*Length.*—5.2 cm.

*Width.*—1.4 cm.

*Color.*—Dark yellow green. (R.H.S. 146B, JHS 3508).

*Thickness.*—0.2–0.4 mm.

*Pubescence.*—Sparse.

*Leaf attaching angle to stem.*—Slanted upward to horizontal.

Flower:

*Facing direction.*—Horizontal.

*Type.*—Single.

*Shape.*—Funnel-shape, with five-fissured limb.

*Shape of petal tip.*—Obtuse to acute.

*Waving of petal.*—Weak.

*Lobation of petal.*—Shallow.

*Diameter.*—2.8 cm.

*Petal.*—Bi-colored. Variegated pattern of petals: Streaked (mist) pattern.

*Base color of bicolored petal.*—Brilliant yellow (R.H.S. 12A, JHS 2505). Color of variegated pattern: Vivid purplish red (R.H.S. 66B, JHS 9707) streaked pattern with slightly dark reddish brown (R.H.S. 166A, JHS 1310) vein. Bottom coloration of the corolla throat: Strong yellow (R.H.S. 11A., JHS 2513) and having slightly dark reddish brown (R.H.S. 166A, JHS 1310) veins. Outside coloration of corolla tube: Light greenish yellow (R.H.S. 4C, JHS 2904) and having slightly dark reddish brown (R.H.S. 166A, JHS 1310) veins.

*Reproductive organs.*—1 normal pistil and 5 normal stamens are attached at the center of the floral tube. All are typical of the species. Viable seeds commonly are formed.

*Peduncle.*—0.7–0.8 mm in thickness, and 1.8 cm in length.

*Duration of blooms.*—The blooms typically last approximately five days on the plant. Pinching is not required to ensure blooming but does serve to enhance the production of blooms.

Physiological and ecological characteristics: High resistance to rain, heat, drought and pests such as mites and aphids, especially the resistance to rain and heat is very strong.

This new variety of Petunia plant 'Sunbelkist' is most suitable for flower bedding and potting, particularly in hanging pots or planters, and further is excellent for planting as a ground cover.

I claim:

1. A new and distinct variety of Petunia plant, substantially as herein illustrated and described, having the following combination of characteristics (A) a semi-decumbent growth habit with long stems, (B) an abundant branching with particularly strong secondary branching, and a great profusion of blooms with the entire plant remaining in bloom for a considerable period of time, (C) flowers that are single and very small with bi-colored petals having a vivid purplish red streak with slightly dark reddish brown veins on brilliant yellow base color with the bottom color of the corolla throat being strong yellow and the outside color of corolla tube being light greenish yellow, and (D) a high resistance to rain, heat, drought and pests such as mites and aphids.

* * * * *